(12) United States Patent
Seliger et al.

(10) Patent No.: US 7,483,908 B2
(45) Date of Patent: Jan. 27, 2009

(54) CONTEXT MANAGEMENT WITH AUDIT CAPABILITY

(75) Inventors: Robert Seliger, Winchester, MA (US); David Fusari, Groton, MA (US)

(73) Assignee: Sentillion, Inc., Andover, MA (US)

( * ) Notice: Subject to any disclaimer, the term of this patent is extended or adjusted under 35 U.S.C. 154(b) by 484 days.

(21) Appl. No.: 11/072,866

(22) Filed: Mar. 4, 2005

(65) Prior Publication Data
US 2005/0165790 A1    Jul. 28, 2005

Related U.S. Application Data

(63) Continuation of application No. 10/014,341, filed on Dec. 11, 2001, now Pat. No. 6,941,313.

(60) Provisional application No. 60/254,753, filed on Dec. 11, 2000.

(51) Int. Cl.
*G06F 17/30* (2006.01)

(52) U.S. Cl. ............... 707/101; 707/104.1; 707/103 R; 705/3; 717/108; 717/101

(58) Field of Classification Search .......... 707/2, 707/5, 6, 9, 1, 101, 103 R–103 Z, 8, 104.1; 705/3; 717/100, 101, 108
See application file for complete search history.

(56) References Cited

U.S. PATENT DOCUMENTS

| | | | |
|---|---|---|---|
| 5,524,238 A * | 6/1996 | Miller et al. ............... | 707/4 |
| 5,566,319 A | 10/1996 | Lenz | |
| 5,878,258 A * | 3/1999 | Pizi et al. ............... | 719/320 |
| 6,134,552 A * | 10/2000 | Fritz et al. ............... | 707/10 |
| 6,397,253 B1 * | 5/2002 | Quinlan et al. ............... | 709/227 |
| 6,401,138 B1 * | 6/2002 | Judge et al. ............... | 719/328 |
| 6,560,655 B1 * | 5/2003 | Grambihler et al. ......... | 709/248 |
| 6,691,118 B1 * | 2/2004 | Gongwer et al. ............ | 707/100 |

OTHER PUBLICATIONS

"Architecture for a Distributed Computing Environment Test Application—Harmonic," IBM Technical Disclosure Bulletin, IBM Corp., New York, NY, vol. 39, No. 6, Jun. 1, 1996, pp. 259-261.
European Examination Report, European Application No. 01 992 074.3.

* cited by examiner

*Primary Examiner*—Cheryl Lewis
(74) *Attorney, Agent, or Firm*—Wolf Greenfield & Sacks, P.C.

(57) ABSTRACT

A context management framework is given that provides in various embodiments, numerous advantages over previously-existing systems. In some instances, an architecture having a centralized storage location coupled to a context manager is provided for servicing and logging context events from a plurality of sources. This type of system uses a synchronization scheme to perform orderly storage and retrieval of data to and from the centralized storage location. In other instances, information stored in the centralized storage location or signals from the context manager are used to achieve an auditing capability for reviewing and acting on context data events and gestures. Selective blocking or allowance of impending context gestures or data-access events is accomplished based on a rule set or lookup table containing rules or other data to make such access-control decisions. Access to private data and other security measures may thus be implemented using the teachings presented herein. Furthermore, a communication paradigm, using a Web-proxy, which identifies ordinarily-unidentified applications to a context manager is provided according to some embodiments of the invention.

60 Claims, 16 Drawing Sheets

CONTEXT MANAGEMENT WITH AUDIT CAPABILITY

REFERENCE TO RELATED APPLICATIONS

This application is a continuation of U.S. Ser. No. 10/014,341, entitled CONTEXT MANAGEMENT WITH AUDIT CAPABILITY, filed on Dec. 11, 2001, which claims the benefit of U.S. Provisional Application Ser. No. 60/254,753, entitled SECURE AUDIT OF USER CONTEXT, filed on Dec. 11, 2000, each of which applications is incorporated herein by reference.

TECHNICAL FIELD

The present disclosure relates generally to data processing systems, and more specifically to context management systems. Yet more specifically, the disclosure relates to context management using a centralized storage location servicing a plurality of applications. Auditing and control of information in a context management setting is also addressed.

BACKGROUND

Context management, sometimes called visual integration, provides a framework, which operates, in conjunction with context-enabled software applications, to streamline and simplify and coordinate the process of accessing stored data and records responsive to actions by a user of the system. If a common attribute is shared between data records to be accessed by the applications, this common attribute, such as log-in information, may need to be repetitively entered into the respective interfaces presented by each application. Since the applications may not come from a single vendor, each application may further have a different interface or may require a different entry by an application user before the application retrieves and presents the data record which the user has asked for.

Many fields of endeavor can benefit from the use of context management. A brief list includes healthcare, sales, government administration, education, and insurance. An attempt has been made in certain industries, for example in the health care industry, to formulate a standard for exchange of context-related information between context-enabled applications. The healthcare industry has developed an industry standard for context management, known as the Health Level Seven (HL7) CCOW standard, having roots in the once-active Clinical Context Object Workgroup. Various versions, beginning with CCOW version 1.0, up to CCOW version 1.4, which is expected to be issued in early 2002, are available. Other later versions can be expected to issue. Each version of the CCOW standard incorporates some features of the previous versions of the standard, and the collection of features that generally describe these versions is hereinafter denoted by the "CCOW standard set" of features.

In a clinical healthcare delivery setting, one application might be directed to patient billing records, and is primarily used by administrators and accountants, while another application that may run on the same platform could present medical image data, for use by physicians and medical professionals. In such cases, a user, for example a patient's primary caregiver, may wish to first view medical record data or medical images for a particular patient, and in the same session view that patient's billing account information or insurance information. Without context management, the primary caregiver would be required to enter data to identify him or herself in order to log in to the various databases containing the desired information, as well as provide patient identifying information so that the particular patient's records may be pulled up in the query. If several such applications are open, it becomes time-consuming and cumbersome to enter the required information and login data into each application's individual user interface. Furthermore, mistakes in typing account numbers or social security numbers, etc., can occur more often when repetitive entry is required.

In order to assist users who are using context-enabled applications, a "context manager" which supports context-enabled applications, is used to pass context data between one application and another. "Context data" is information indicative of a condition or identity associated with users, applications, stored records, or any other information that facilitates or enables performance of inter-application or inter-platform functionality in a context management environment. The context data may contain data useful for accessing data relating to or identifying an attribute of a user, machine, application, customer, or patient.

By carrying out certain actions, referred to as "context gestures," a user using a context-managed environment causes context data to be generated and transmitted through the context manager. The context gestures may take any of numerous forms, but generally are responsive to a need by the user to move between applications or windows executing in a data processing system. The context in which the gestures are carried out may be transmitted from a first application to a second application to simplify the work of the user, as described above, so that the second applications "knows" what context the user is working in at the time the user shifts from using the first to using the second application. This looking-ahead functionality is a shortcut that shifts some of the burden of cross-application work from the user to the context manager.

A typical implementation of a context management system according to the prior art is shown in FIG. 1. A context manager 100 is coupled to a plurality of context-enabled applications 110. Sometimes, a log 112 of activity associated with a particular application 110 is maintained by the applications 110. Since the logging capability is conventionally provided by the vendor of the particular application, e.g. 110a, the application log, e.g. 112a, is in a format selected by the vendor for the logging purpose. An application log 112 may contain application data in a proprietary data format, or may include or exclude certain types of log information, as designed by the application vendor. Conventionally, no consistency or standardization or compatibility is expected or maintained between one application log, e.g. 112a, and another application log, e.g. 112b. Other software applications, including the context manager 100, can thus not make use of application logs 112 unless specifically configured for particular expected formats and content.

As more records are kept in electronic form and as the types of information retained in databases has proliferated, a concern has developed regarding the security and privacy of such information. Privacy rights are an important factor in the design and operation of commercial, governmental, educational, financial and medical record keeping systems. Legislation has been passed in some instances to protect consumer and patient records for example, and liability attaches to maintaining and using such data.

The medical industry in particular views the safety and privacy of patient records as a public policy issue. The Health Insurance Portability and Accountability Act of 1996 (hereinafter "the HIPAA") was passed by Congress to address such public policy issues, and lays out guidelines and requirements for institutions and entities in control of patient records and data.

Presently, no satisfactory and efficient way is known to enable monitoring, auditing, enforcing or assessing compliance with local institutional policies or government regulations, especially across applications or platforms. Also lacking is any consistent approach to recording or controlling access to such sensitive data across applications executing on a data processing system. The absence of centralized logging and storage means useful to a broad spectrum of applications from a plurality of software application vendors is a continuing problem that hinders or prevents streamlined data access management or auditing.

SUMMARY

Accordingly, some embodiments of the present invention are directed to a method for auditing data-access events occurring in a context management system, the method comprising: collecting context data from a plurality of applications that use the context management system; storing data corresponding to the collected context data on a centralized storage location; and extracting audit information by processing at least a subset of the data stored on the centralized storage location.

Other embodiments are directed to a method for storing context data, from a plurality of sources in a context management system, onto a centralized storage location, comprising: receiving context data from the plurality of sources; synchronizing the context data using a context manager; and storing the context data in the centralized storage location; wherein storing the context data is performed according to a synchronization scheme, that includes context data from at least two sources.

Another embodiment is directed to a method for controlling access to a stored data object, comprising: determining whether a data-access event is authorized under a predetermined rule, wherein a context manager is operable to allow or deny execution of said data-access event based on (i) context data, corresponding to the data-access event, and (ii) the predetermined rule.

Regarding the Health Insurance Portability and Accountability Act (HIPAA), some embodiments are directed to a method for assessing compliance with the HIPAA, in a context management system, the method comprising: collecting context data from a plurality of applications that use the context management system; storing data corresponding to the collected context data on a centralized storage location; and extracting audit information by processing at least a subset of the data stored on the centralized storage location, the audit information suitable for making an assessment of compliance with a provision of the HIPAA.

Additionally, some embodiments are directed to a method for auditing data access events in a data processing system, comprising: transferring context information from a first software application executing in the data processing system to a second software application executing in the data processing system; storing the context data in a centralized storage location; and extracting from the centralized storage location information indicative of data access events occurring in the data processing system.

Yet other embodiments are directed to a data processing system for auditing data access events in a context management framework, comprising: a plurality of software applications executing in the data processing system; a context manager coupled to the software applications that manages context data exchanges between the software applications; a centralized storage location, coupled to the context manager, that stores a central record of the context data exchanges; and an auditor, coupled to the centralized storage location, that retrieves information from the centralized storage location indicative of data access events occurring in the data processing system.

According to some embodiments, a machine-readable medium is provided, having thereon instructions, which when executed: collect context data from a plurality of applications that use a context management system; store data corresponding to the collected context data on a centralized storage location; and extract audit information by processing at least a subset of the data stored on the centralized storage location.

Yet other embodiments are directed to a method for identifying an application in a context management environment, wherein the application is coupled to a context manager, comprising: associating the application with an information tag when the application invokes a method that carries application-identifying information; augmenting a URL, passing between the context manager and the application, with the information tag, yielding a compound URL containing the URL and the information tag; parsing a communication from the application containing the compound URL to extract information corresponding to the information tag therefrom when the application invokes a method that does not carry application-identifying information; and looking up the identity of the application corresponding to the information tag.

DETAILED DESCRIPTION

Figure 1:
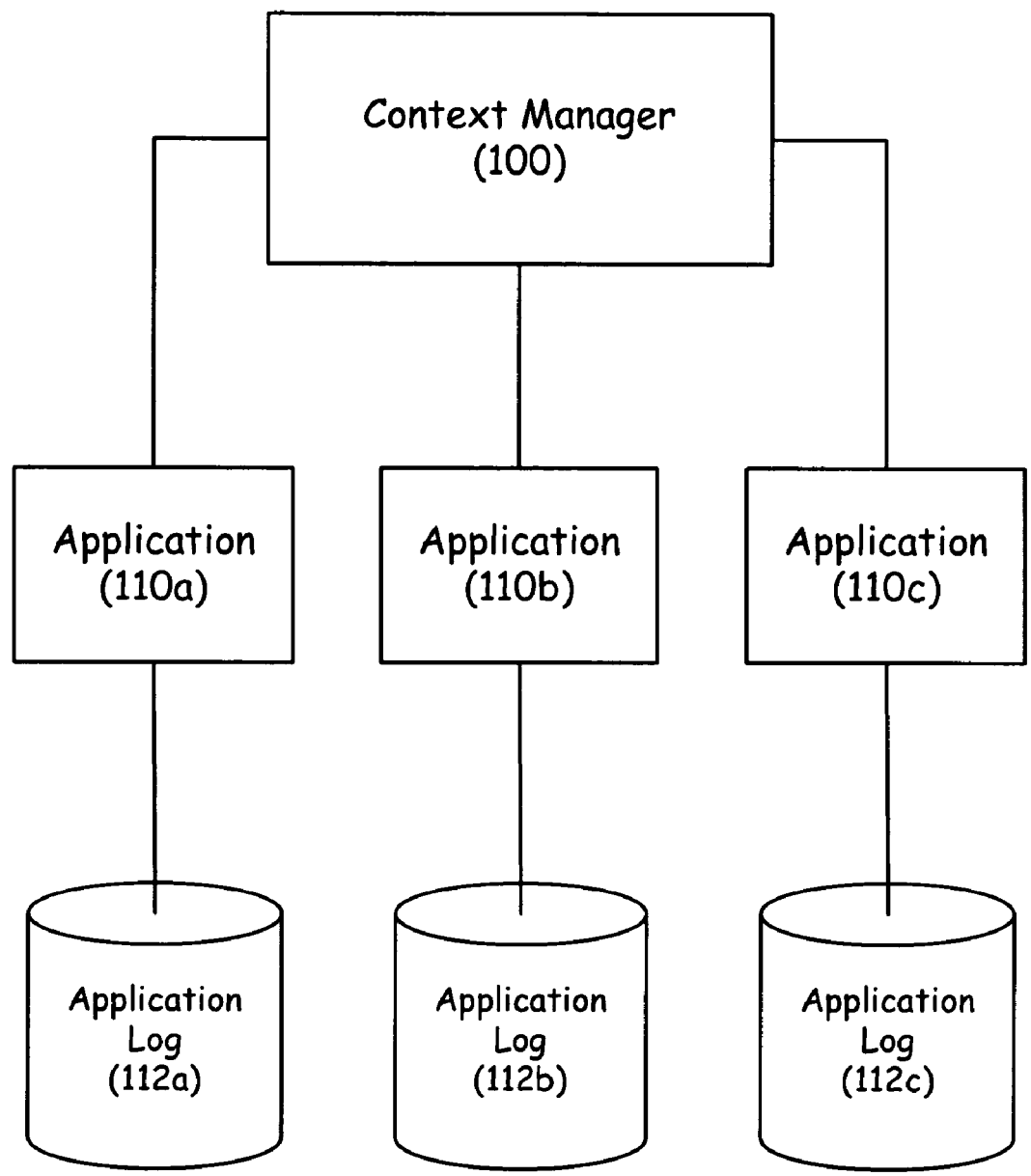
FIG. 1 shows a context management system according to the prior art.

Various aspects of embodiments of the present invention address and remedy various shortcomings of presently-available systems either mentioned previously or as will become apparent to those skilled in the art upon review of this disclosure. Generally, control and auditing capabilities are provided for context management, and various other features and enhancements are also provided by the present context management architecture, to be described in more detail below. A non-exhaustive description of several aspects of embodiments of systems and methods follow, including a centralized storage architecture for context management, auditing of data from the centralized storage location, sometimes coupling the centralized storage location to the context manager over a network, synchronizing context data for delivery to and retrieval from the centralized storage location, collecting context data at intermediate collection platforms or message queues and buffers for use with the centralized storage architecture, and controlling access to data records and/or context data logged on the centralized storage location.

Many shortcomings of the prior art are remedied by use of a centralized storage location coupled to the context manager. While it is possible to still use the application-specific logs and application data records in their specialized or proprietary formats, the centralized storage coupled to the context manager enhances the functionality and usefulness of the context manager. In some embodiments, added capabilities are introduced as a result of having a consistent monolithic record of context events and data-access events in the centralized storage location. Examples of these added capabilities include multiple-application audit capability and access control.

The nature of the present invention will become apparent upon reading the description of the aspects of embodiments thereof, and especially when read in conjunction with the associated figures in which like elements are denoted by like reference numerals.

Figure 2:
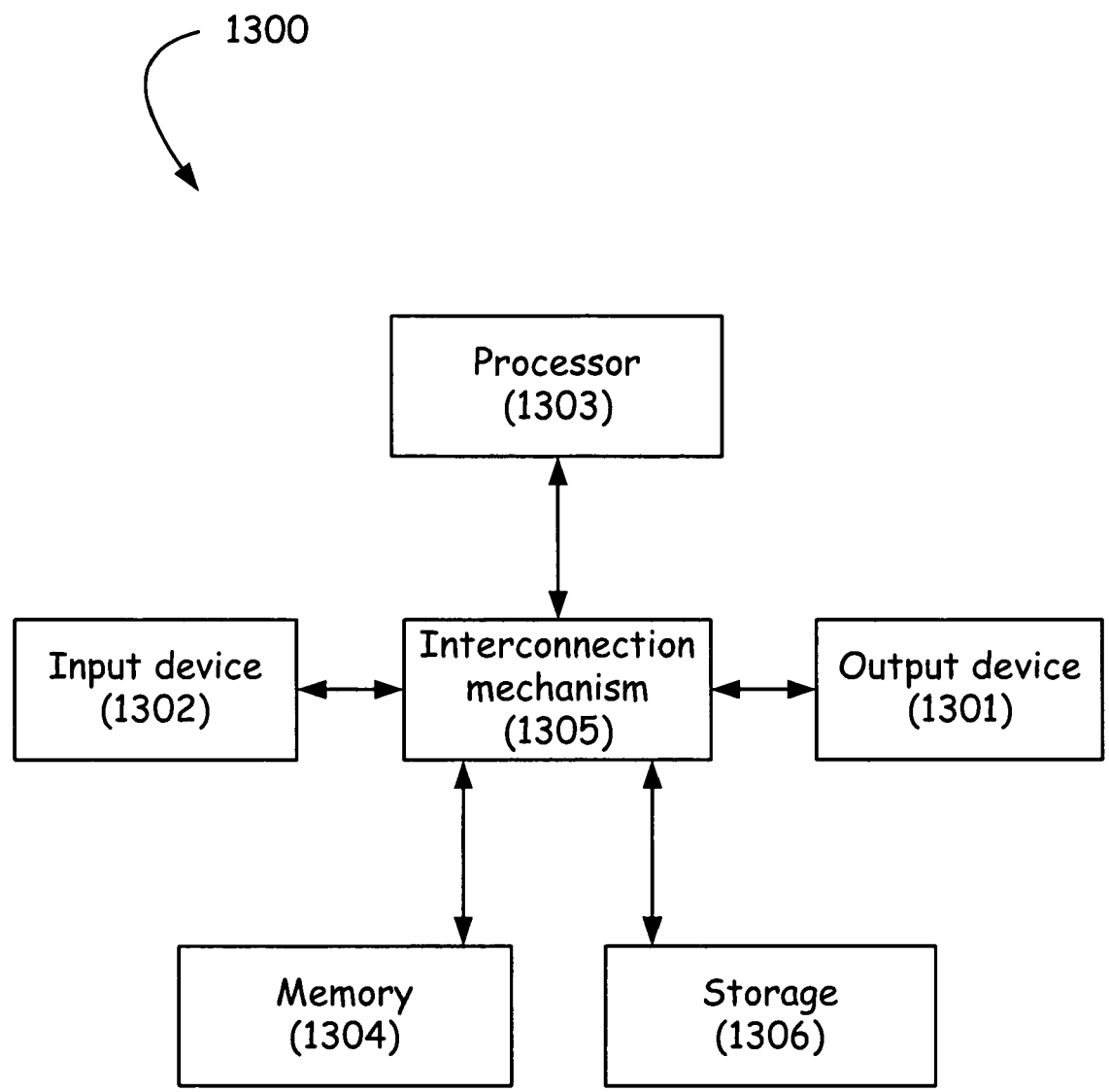
FIG. 2 shows an exemplary data processing computer system and its primary components.

In some preferred embodiments, aspects of the present invention are carried out on a data processing system or on a computer system. A computer system 1300, is shown in FIG. 2. Various elements of the embodiments described herein, either individually or in combination, may be implemented on the computer system 1300. Typically the computer system 1300 includes at least one main unit coupled, directly or indirectly, to one or more output devices 1301 which transmit information or display information to one or more users or machines. The computer system 1300 is also coupled, directly or indirectly, to one or more input devices 1302 which receive input from one or more users or machines. The main unit may include one or more processors 1303 coupled, directly or indirectly, to a memory system 1304 via one or more interconnection mechanisms 1305, examples of which include a bus or a switch. The input devices 1302 and the output devices 1301 are also coupled to the processor 1303 and to the memory system 1304 via the interconnection mechanism 1305. The computer system 1300 may further comprise a storage system 1306 in which information is held on or in a non-volatile medium. The medium may be fixed in the system or may be removable.

The computer system 1300 may be a general purpose computer system which is programmable using a computer programming language. Computer programming languages suitable for implementing such a system include procedural programming languages, object-oriented programming languages, macro languages, or combinations thereof. The computer system 1300 may also be specially-programmed, special-purpose hardware, or an application specific integrated circuit (ASIC).

In a general-purpose computer system, the processor 1303 is typically a commercially-available processor which executes a program called an operating system which controls the execution of other computer programs and provides scheduling, input/output and other device control, accounting, compilation, storage assignment, data management, memory management, communication and data flow control and other services. The processor and operating system define the computer platform for which application programs in other computer programming languages are written. The invention is not limited to any particular processor, operating system or programming language.

Figure 3:
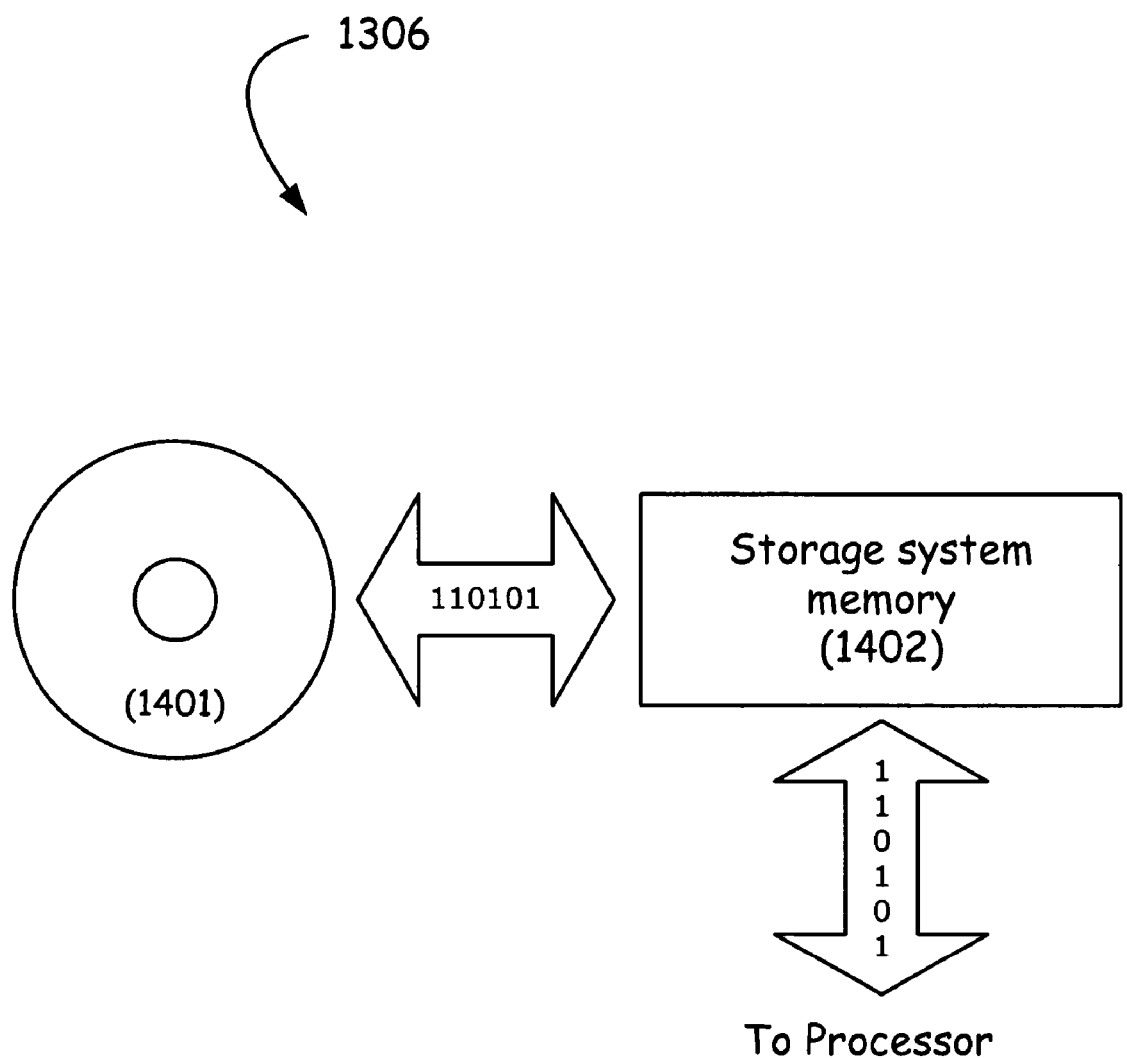
FIG. 3 shows an exemplary storage system which can be used with the computer system.

The storage system 1306, shown in greater detail in FIG. 3, typically includes a computer-readable and writeable non-volatile recording medium 1401 in which signals are stored that define a program to be executed by the processor 1303 or information stored on or in the medium 1401 to be used by the program. The medium 1401 may, for example, be a disk or flash memory. Typically, in operation, the processor 1303 causes data to be read from the nonvolatile recording medium 1401 into another memory 1402 that allows for faster access to the information by the processor 1303 than does the medium 1401. This memory 1402 is typically a volatile, random access memory (RAM), such as a dynamic random access memory (DRAM) or static random access memory (SRAM). It may be located in storage system 1306, as shown in FIG. 3, or in memory system 1304, as shown in FIG. 2. The processor 1303 generally manipulates the data within the integrated circuit memory 1304, 1402 and then copies the data to the medium 1401 after processing is completed. A variety of mechanisms are known for managing data movement between the medium 1401 and the integrated circuit memory element 1304, 1402, and the invention is not limited thereto. The invention is also not limited to a particular memory system 1304 or storage system 1306.

Aspects of embodiments of the invention may be implemented in software, hardware, firmware, or combinations thereof. The various elements of an embodiment, either individually or in combination, may be implemented as a computer program product including a computer-readable medium on which instructions are stored for access and execution by a processor. When executed by the computer, the instructions instruct the computer to perform the various steps of the process.

Figure 4:
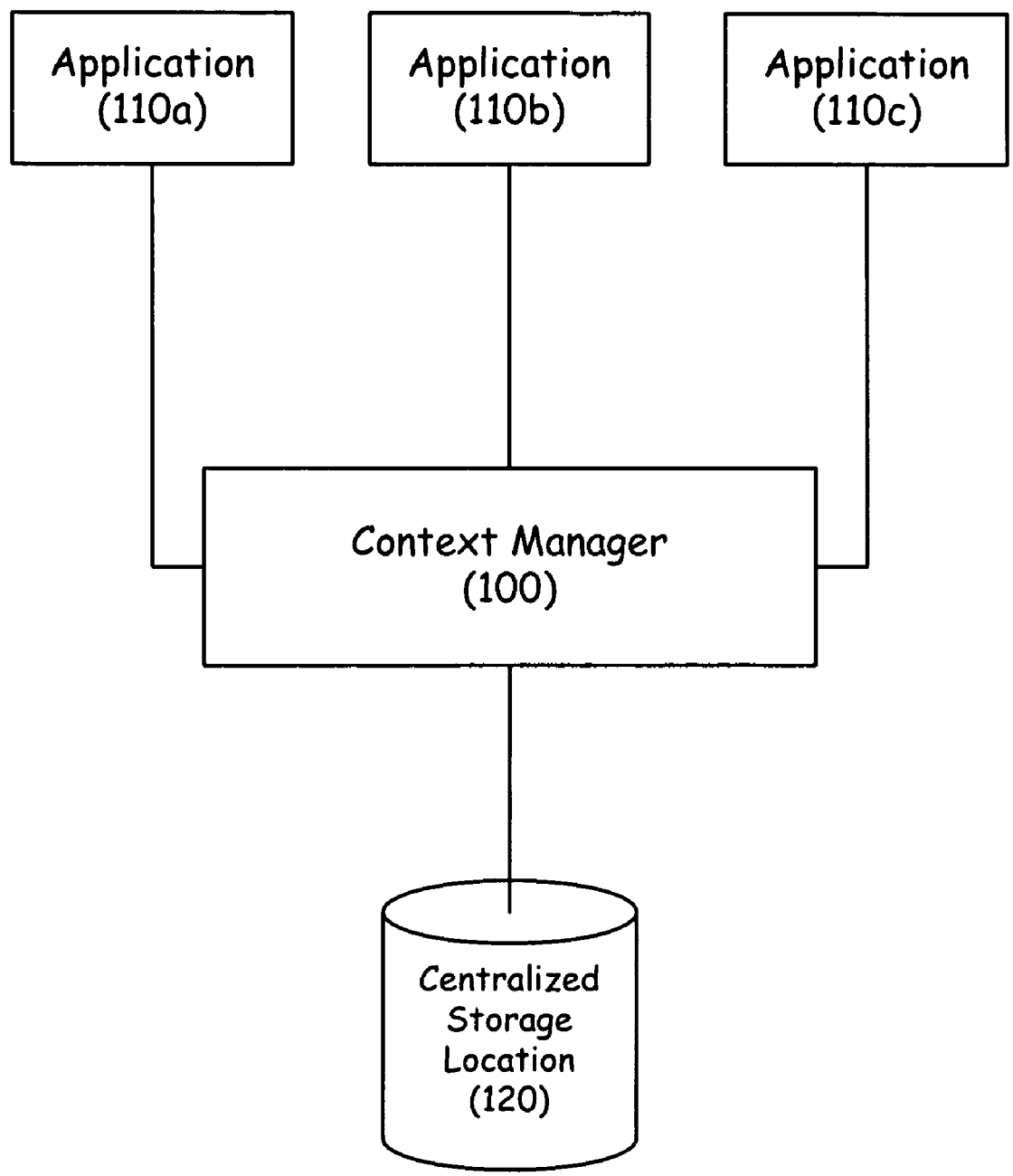
FIG. 4 shows an embodiment of a context management system according to the present invention.

FIG. 4 shows an embodiment of a context management architecture which places the context manager 100 in between a plurality of context-enabled applications 110 and a centralized storage location 120. This architecture allows for a streamlined uniform storage and access capability by the context management system. Note that applications 110 may retain and use their individual dedicated logs 112, as described earlier with reference to FIG. 1. In some embodiments, not all the data needed for some purpose will be store in the centralized storage location 120, in which case the application logs 112 can be useful in providing functionality or data to augment information from the centralized storage location 120. In order to achieve the architecture shown in FIG. 2, some embodiments use a context management server (sometimes referred to as a "vault" or an "appliance") or other component of the context manager 100 to act as a collector for context data passing to and from various applications 110. Once collected, context data may be sent through message queues and/or synchronizers to the centralized storage location 120. Reference is made to U.S. patent application Ser. Nos. 60/136,670, 60/139,235, 60/254,753, 09/545,396 and 09/583,301, which provide disclosure of subject matter related to context management systems, and all of which are hereby incorporated by reference.

The centralized storage location 120 may be structured, and organized according to any of numerous ways known to those skilled in the art of data storage. Examples of the centralized storage location 120 include file systems and databases. Databases suitable for use with the present invention include, but are not limited to, relational databases, hierarchical databases, networks and directory systems. The information kept on the centralized storage location 120 may be formatted or modified for example by compression to improve economy or using another data processing technique to improve efficiency or performance of the storage system.

It should be noted that the data stored on the centralized storage location 120 is not constrained to explicit storage of context data per se. The data stored on the centralized storage location 120 may be data corresponding to the context data or parts thereof. That is, a formatter or data translator may be employed in the context manager 100 and/or in the centralized storage location 120 which is adapted to convert data from one data format to another. For example, in a system supporting the CCOW standard set and data compatible therewith, a formatter 230 may be employed to convert data between a first data format and a second format compatible with the CCOW standard set.

Figure 5:
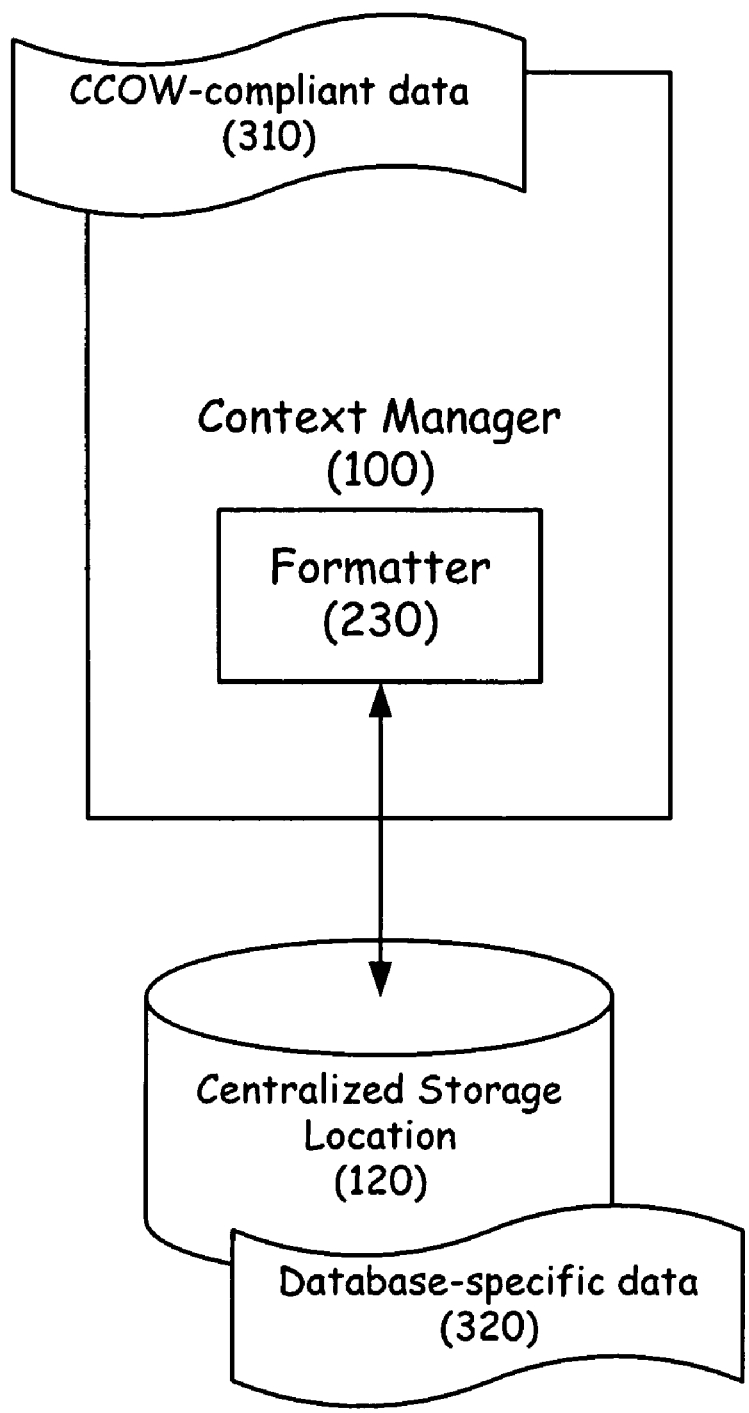
FIG. 5 shows an embodiment of a context management system where data is formatted between two formats using a formatter.

FIG. 5 shows a formatter 230 disposed between the context manager 100 and the centralized storage location 120. CCOW-compliant data 310 is used in the context management system by the context manager 100, but the centralized storage location 120 only sends and receives data 320 formatted in a database-specific data format. The formatter 230 may be implemented in the context manager 100 or in another component suitable for carrying out the formatting operations.

It should also be understood that some communication events and data transfer events carried out according to some aspects of embodiments of the present invention may be done securely. Secure communication between any of the components, applications, or storage devices may be optionally implemented as a mode of operation, thus allowing non-secure and secure context management operations.

Further, the applications 110 may still remain coupled to their respective individual vendor-specific logs 112 as described earlier.

Figure 6:
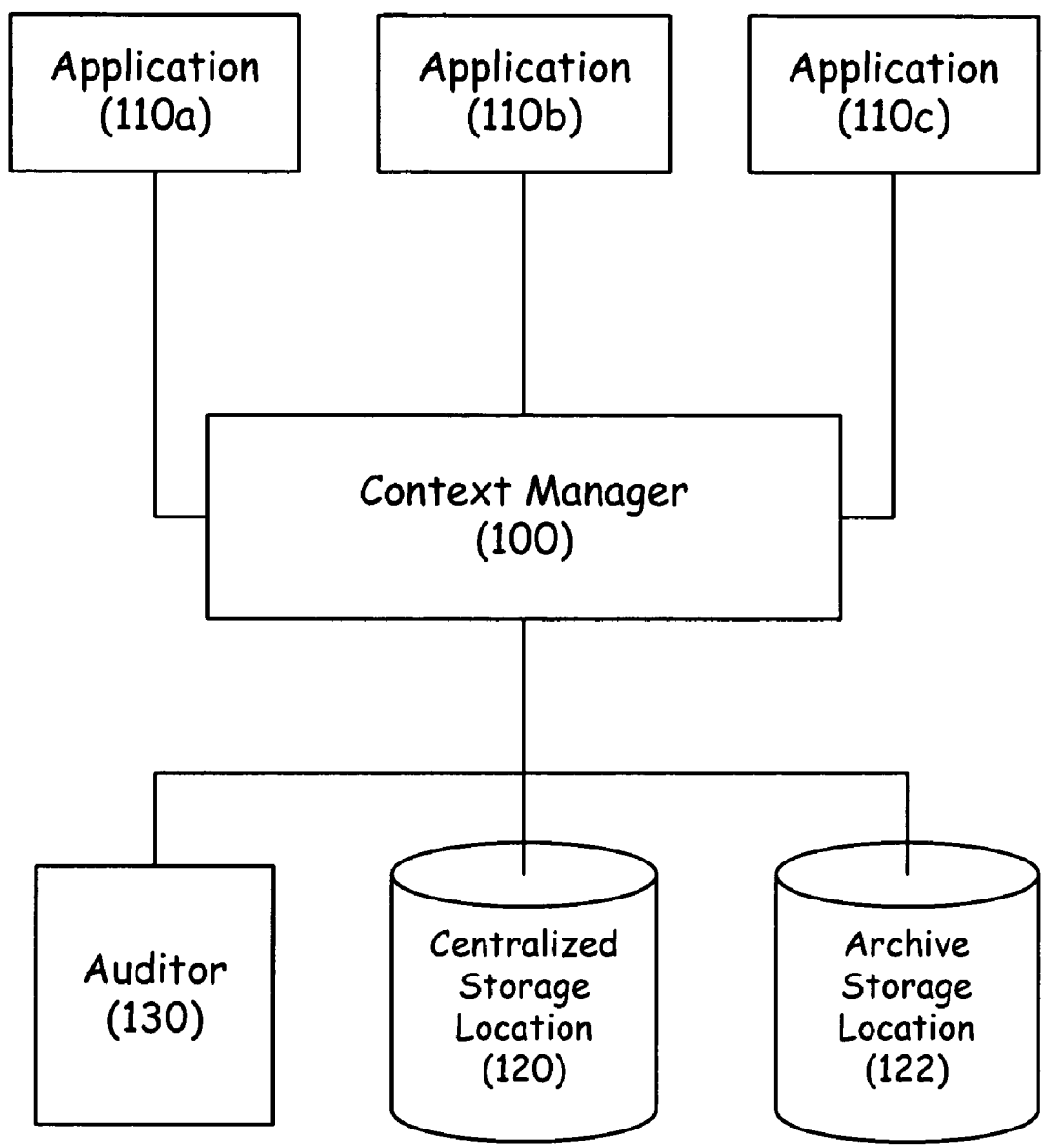
FIG. 6 shows an embodiment of a context management system according to the present invention, including audit and archive capability.

FIG. 6 shows an embodiment of a context management system as described above, but further having an archive storage location 122 coupled to the centralized storage location 120. While configurable in many ways, an archive can serve to relieve the primary centralized storage location 120 of old data, or data not in active use, allowing the centralized storage location 120 to delete or overwrite old or unused data. Since context management systems can be expected to accumulate a large amount of stored information over time, archival capability may become necessary if the centralized storage location 120 nears or reaches its capacity. The archive storage location 122 can then in turn be coupled to other backup or auxiliary archive devices, such as tapes, digital storage media, or other printed or electronic forms of record keeping. The archive storage location 122 does not necessarily reside in any predetermined location or arrangement relative to the centralized storage location 120. In fact, the archive storage location 122 may be implemented as a plurality of storage locations which may be distributed or only temporarily coupled to the overall system for transfer of data from the centralized storage location 120 back and forth to the archive storage location 122.

It is often, but not always, necessary to have the system be able to transfer data both to and from the archive storage location 122 when necessary. Thus it is useful in some cases to incorporate retrieval capability to retrieve archived data from the archive storage location 122 back into the centralized storage location 120 for use by the context manager 100 or other elements coupled thereto.

The embodiment of FIG. 6 also shows an auditor 130 coupled to the centralized storage location 120. The auditor is capable of accessing and processing data from the centralized storage location 120. As an example of the many possible uses for the auditor 130, periodic audits by the auditor 130 can be conducted to assess an organization's compliance with local organization policies or its adherence to statutory requirements. As a specific example, a hospital using a context management system and having a centralized storage location 120 may conduct periodic audits using the auditor 130 to parse through context data or other data stored on the centralized storage location 120. Such audits may be conducted by the auditor 130 or another auxiliary module coupled thereto, and send summary reports or other conclusory information to an output device or to another machine or to another destination that can make use of and interpret such information.

The auditor 130 may be equipped with software to generate automatic reporting sheets, signals, tables, or data objects indicative of the organization's compliance with its own policies or with applicable laws. Additionally, detailed reports on the usage of a hospital's patient medical records or accounting records by particular users may be generated. If a particular hospital employee comes under suspicion for acting in a way that is in violation of the policies or laws mentioned above, an audit can be performed, including an audit report, containing information showing which context data was associated with that employee. This information may then reveal whether or not the employee improperly accessed certain information or used certain applications in violation of applicable policies and rules as described above.

Similarly, an audit may be performed and an audit report generated to indicate what context-related activity has taken place on the system relevant to a particular patient's records. According to one aspect of this embodiment, the centralized storage location 120 stores such information in a way which is searchable and cross-referenced. Therefore the auditor 130 can generate a variety of customized audits depending on the need.

It is important to mention that the process of collecting, storing, or subsequently auditing information is not limited to collecting, storing and auditing context data. Data-access events generally are so recordable and auditable. These data-access events can comprise any of at least: context data, certain types or subsets of context data (i.e. not all available or collected context data), context data items (e.g., user, patient), context gestures, application data access, and attempted data-access events (insofar as they are identifiable and translate into meaningful signals). Thus a "data-access event" is almost any event corresponding to an action by a user or a machine which causes data (including context and application data) to be moved from one location to another or to be retrieved from memory.

In addition, not all of the collected context data needs to be stored into the centralized storage location 120. In some instances only a subset of the context data is stored. Considerations of computational resources, execution speed, efficiency and privacy may influence the decision on what context data to collect or store.

Figure 7:
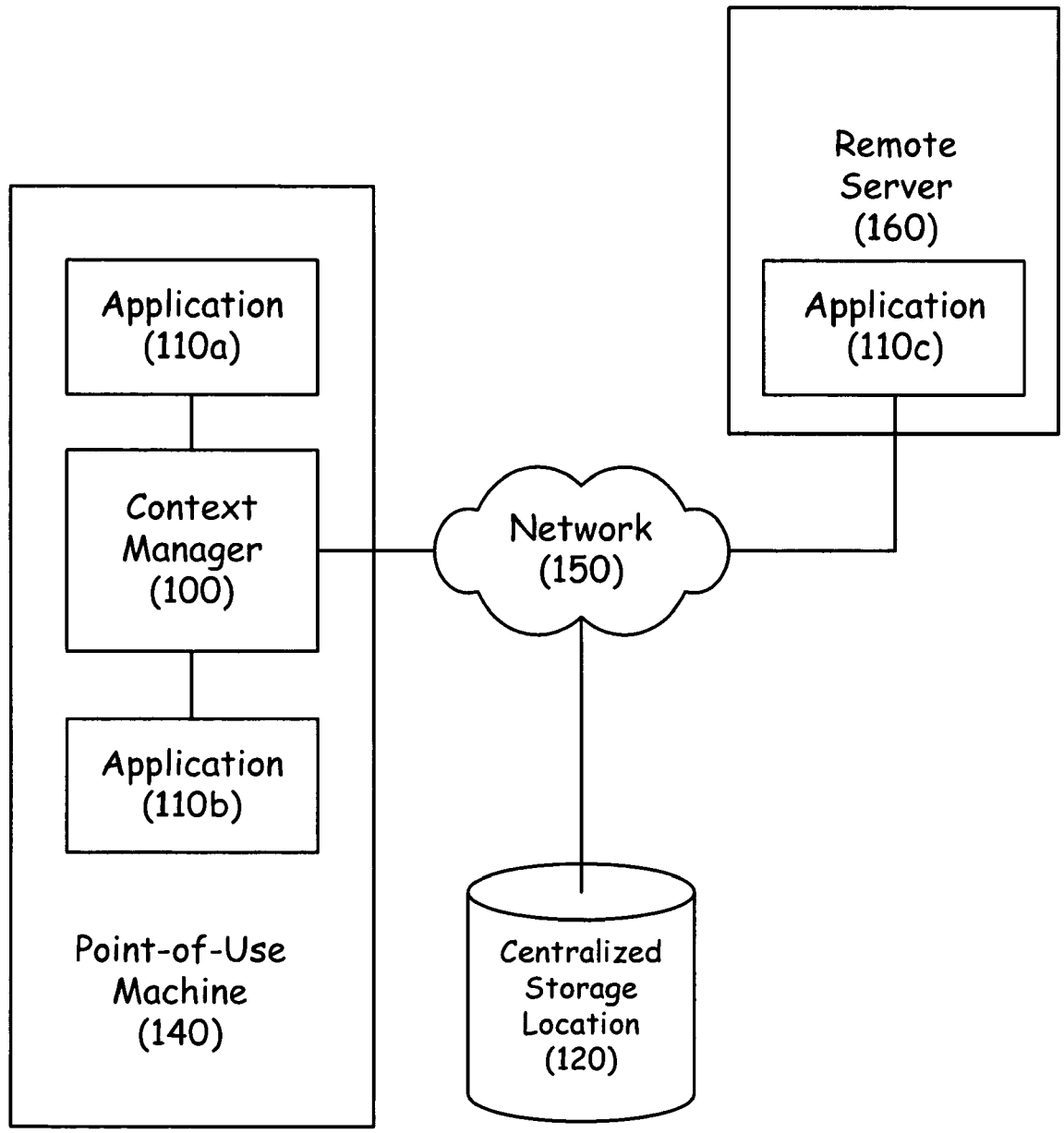
FIG. 7 shows an embodiment of a context management system having some applications executing on a point-of-use machine and others executing on a remote server, with a network coupling various components of the system.

FIG. 7 shows an embodiment of a context management system having an architecture using a network 150 adapted for carrying communication signals, data, and other information from one location to another. While still employing the context manager 100 to conduct context transactions between a plurality of applications 110, the applications 110 may not all be executing on the same machine on which the context manager 100 runs. Thus, if the context manager 100 is executing on a point-of-use machine 140, and applications 110a and 110b are also executing on the point-of-use machine 140, a third application 110c may execute on a remote server 160, coupled to the point-of-use machine 140 and the context manager 100, by a network 150. The context manager 100 may also use the network 150, or another network coupled thereto, to reach the centralized storage location 120.

Secondary or auxiliary networks and other machines may be connected in a complex architecture as is known to those skilled in the art of networking. In fact, an entire enterprise (e.g., a hospital) may be coupled to a few or even a single context manager 100. The entire enterprise may then use the services of the centralized storage location 120. Various considerations, including reliability and security, may dictate using a number of storage locations, which when taken together form the centralized storage location 120. It is not necessary to have a single disk drive or tape device or other storage device acting as the centralized storage location 120. Instead, it is possible to employ subsystems, which need not be of the same type, to serve as the centralized storage location 120.

The context manager 100 itself may run as a software application executing on a local point-of-use machine 140, or may be executed as an applet in a frame on the desktop of the point-of-use machine 140. The context manager 100 may itself be executing on a remote web server such as the remote server 160.

The ability to access and audit the contents of the centralized storage location 120 opens up new possibilities for enhancing the functionality of context management systems. Since the data stored on the centralized storage location 120 is uniformly-accessible to the auditor 130, the auditor 130 may trigger, based on some criterion, a particular subsequent decisional act. For example, a decision can be made automatically or by a "monitor," which can be a human or a machine, that acts or is informed upon execution or attempted execution of a certain context gesture. As an example, a member of a hospital's accounting department may not have authorization to access patient medical records. A determination of such access may be made by comparing an attribute of the user who is logged into the system with a list of attributes of those forbidden to access patient medical records. A code or other identifying feature, such as user name or employee ID number, can be compared with an index of hospital employees who are allowed to access patient medical records. Even more specifically, it may be decided by local policy that only physicians treating particular patients may have access to those particular patients' medical records. Analogously, a physician handling one aspect of a patient's healthcare, e.g., respiratory conditions, may be barred from modifying or accessing patient medical records having to do with the patient's other medical conditions, e.g., mental health.

It is possible, based on output from the auditor 130, to then trigger a message to the user informing the user of a particular condition. For example, an alert may be presented to a caregiver if a certain patient has a medical condition warranting special care in certain circumstances. As a specific example, a pharmacy employee at the hospital who conducts a context gesture to fill a prescription for a certain patient may be presented with a message reciting known allergies for that particular patient. The warning message or alarm may be triggered by the pharmacy employee performing a context gesture that involved the particular patient with the allergies. That is to say that the present invention provides, in some embodiments facilitating audit and/or context-driven controls, for decisional and other actions to be undertaken or initiated based on context data.

Output from the auditor 130 may be sent to a machine or human monitor, who will take some action in the event that a certain unauthorized data access event has taken place or an attempt to perform such an unauthorized act has taken place. A more complete description of embodiments using a monitor will be given below.

Figure 8:
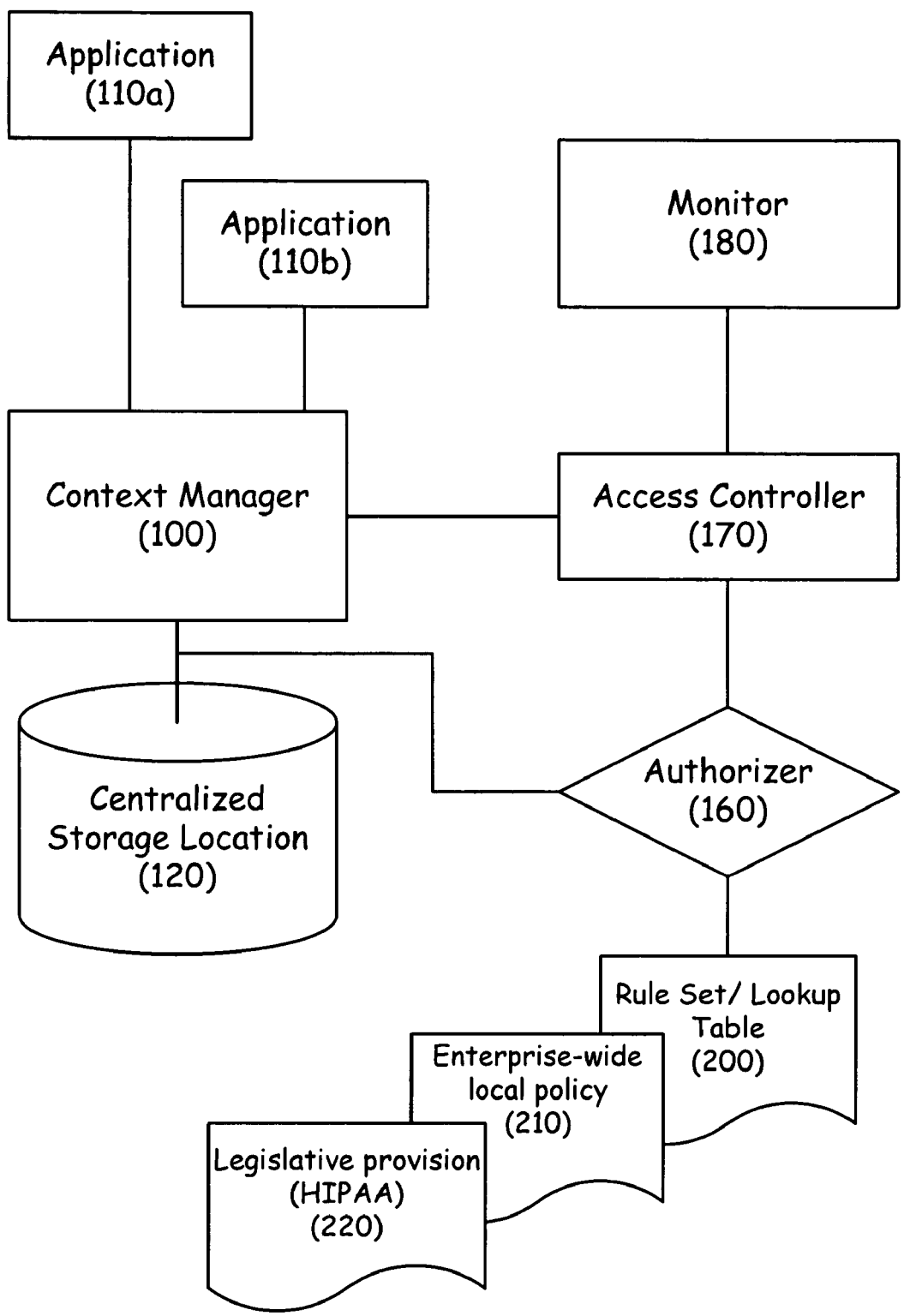
FIG. 8 shows an embodiment of a context management system which uses a rule set to control data-access events by a user, the figure also shows a monitor coupled to the system.

Authorization and access control may be conducted with or without an auditor 130. FIG. 8 shows an embodiment of a context management system having authorization and access control capability. In this example, a plurality of applications 110 exchange context data through a context manger 100 as before. The context manager 100 may be coupled to a centralized storage location 120 as described earlier, and other features of that architecture as described above are possible. However, in this embodiment, an authorizer 160 receives context data or data corresponding to context gestures and performs a determination of whether the context gestures are authorized. The authorizer 160 has access to look-up tables or rule sets 200 to make the decision whether a context gesture is authorized or not. The rule set or look-up tables 200 may be coupled to or incorporate enterprise-wide local policy rules or tables 210 and legislative provisions or statutes or other rule-based criterion 220.

The concept given above may be generalized so that rule-based decisions include all means for arriving at a decision. A "rule" can hence be considered for our purposes to encompass at least: an algorithmic or logical operation, a table whose contents form a rule, etc. A look-up table (LUT) is an example of such a rule, usually stored in memory. An algorithm for making a decision on the basis of a mathematical calculation is another rule accessible to a context management system.

The authorizer 160 provides an output to an access controller 170 which is adapted for controlling permission to perform a context gesture or other act. If authorization is declined by the authorizer 160 for a particular context gesture, the access controller 170 may send or decline to send a signal to the context manager 100, implementing the access control decision. Alternately, a signal containing the results of an authorization check can be sent to the context manager 100, which will then implement the access control. The context manager 100 may accomplish this by incorporating sub-modules which implement the functions of the authorizer 160 and/or the access controller 170 as described above. However, this functionality may also be built into other modules which may execute on any of the machines in the context management system.

Once a decision is made on whether to allow a particular context gesture, this often implies a determination of whether the associated data record access is authorized and can be carried out. In our previous example, an accountant who is attempting to access a patient's mental health records may be barred from viewing the medical record as a consequence of being barred from executing the corresponding context gesture.

In addition to merely denying or allowing the execution of a context gesture or a data record access event, the access controller 170 and/or authorizer 160 may provide a signal to a monitor 180. The monitor 180 may itself cause or send signals, such as alarm signals or signals that shut down a system or activate another system. The monitor 180 may be implemented in numerous ways. These include implementation as an electronic mail server adapted to sending an electronic mail message to an administrator, alerting the administrator of a breech. The monitor 180 may similarly be a telephony or paging server, adapted for delivering a telephone or pager message to an administrator or other security personnel. The monitor 180 may in addition be an alarm device, such as an audible or a visual alarm. The monitor 180 can also be a human operator who can make decisions based on an alarm signal or other message from the monitor 180.

In some embodiments, the authorizer 160 may be coupled to the centralized storage location 120, and receive its input from the centralized storage location 120 rather than from the context manager 100.

Figure 9:
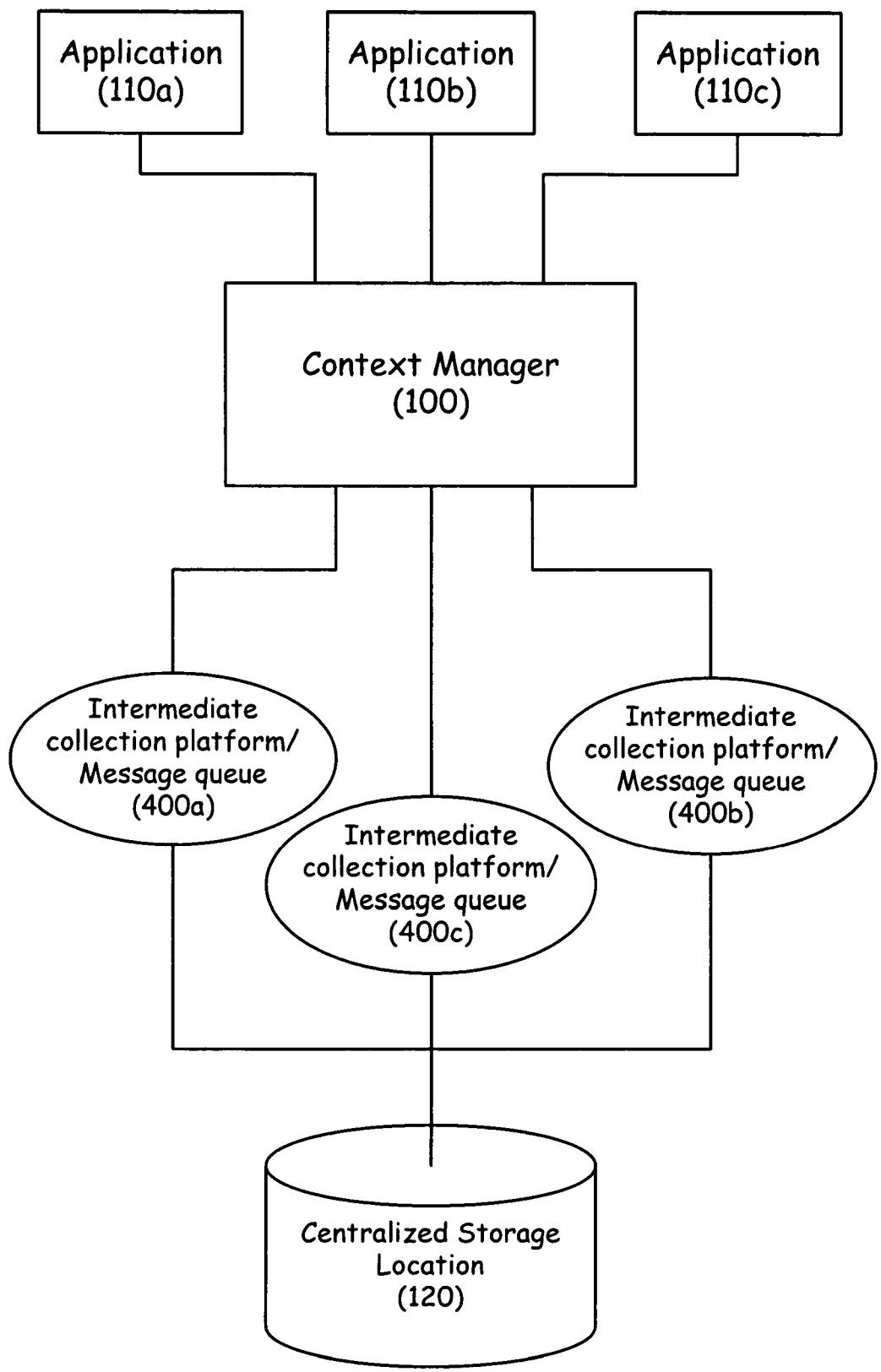
FIG. 9 shows an embodiment of a context management system having intermediate collection platforms or message queues.

FIG. 9 shows an embodiment of a context management system employing intermediate collection platforms 400 and/or message queues. The context-enabled applications 110 exchange context data through the context manager 100. The intermediate collection platforms may be storage locations or buffers, implemented in hardware and/or in software, optionally as part of the context manager 100. The intermediate collection platforms may comprise message queues. The message queues are in turn coupled to the centralized storage location 120.

Many other architectures, including distributed architectures at the local and global level, may add functionality to the system and methods described by the present invention.

Figure 10:
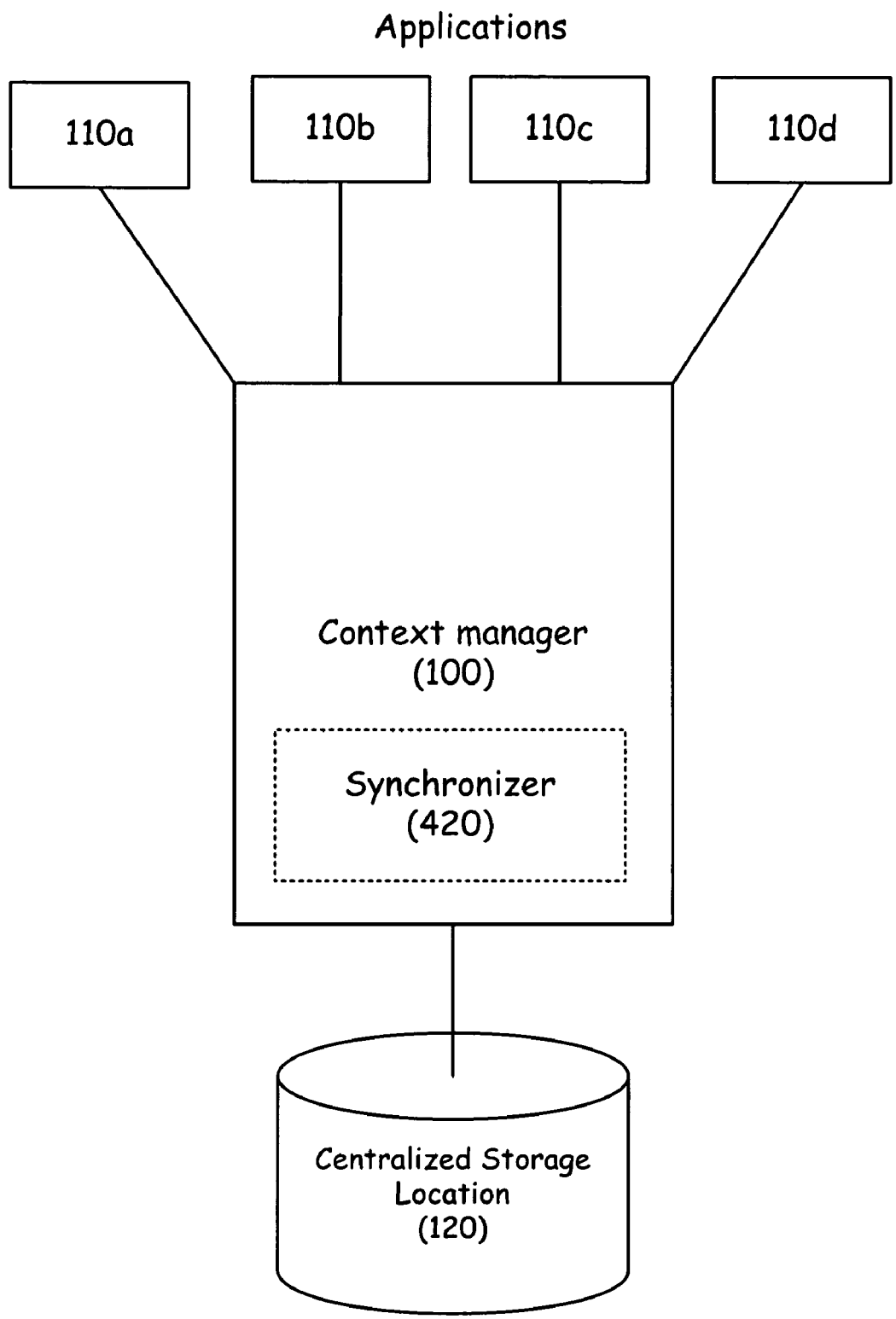
FIG. 10 shows an embodiment of a synchronizer in a context management system which synchronizes context data for storage on a centralized storage location.

FIG. 10 shows a synchronizer 420, which may be implemented separately or as part of a context manager 100, for use in a context management system. A plurality of applications 110 receive and send context data to the synchronizer 420. In order to effect a smooth and organized storage onto and retrieval from the centralized storage location 120, the synchronizer 420 uses a synchronization scheme adapted for organizing the incoming context data into a single stream of data for storage onto the centralized storage location 120. The synchronization scheme may comprise a chronological scheme, wherein messages and data arriving at the synchronizer 420 are placed in the proper order for storage on to the centralized storage location 120. Tags appended to, or other criterion can be used as synchronizing schemes.

One aspect of this exemplary embodiment of the present invention is that it allows for a scaleable architecture. It can be especially advantageous in enterprise-wide systems to have context management with a centralized storage location 120 as described above. However, if the number of machines, including servers and point-of-use machines proliferates, it may be efficient to carry out the clustering described herein so that the overall architecture remains compatible with the concept of centralized storage. As described previously, the centralized storage location 120 itself may be clustered or formed of smaller sub-systems that are then organized logically using a single index.

Figure 11:
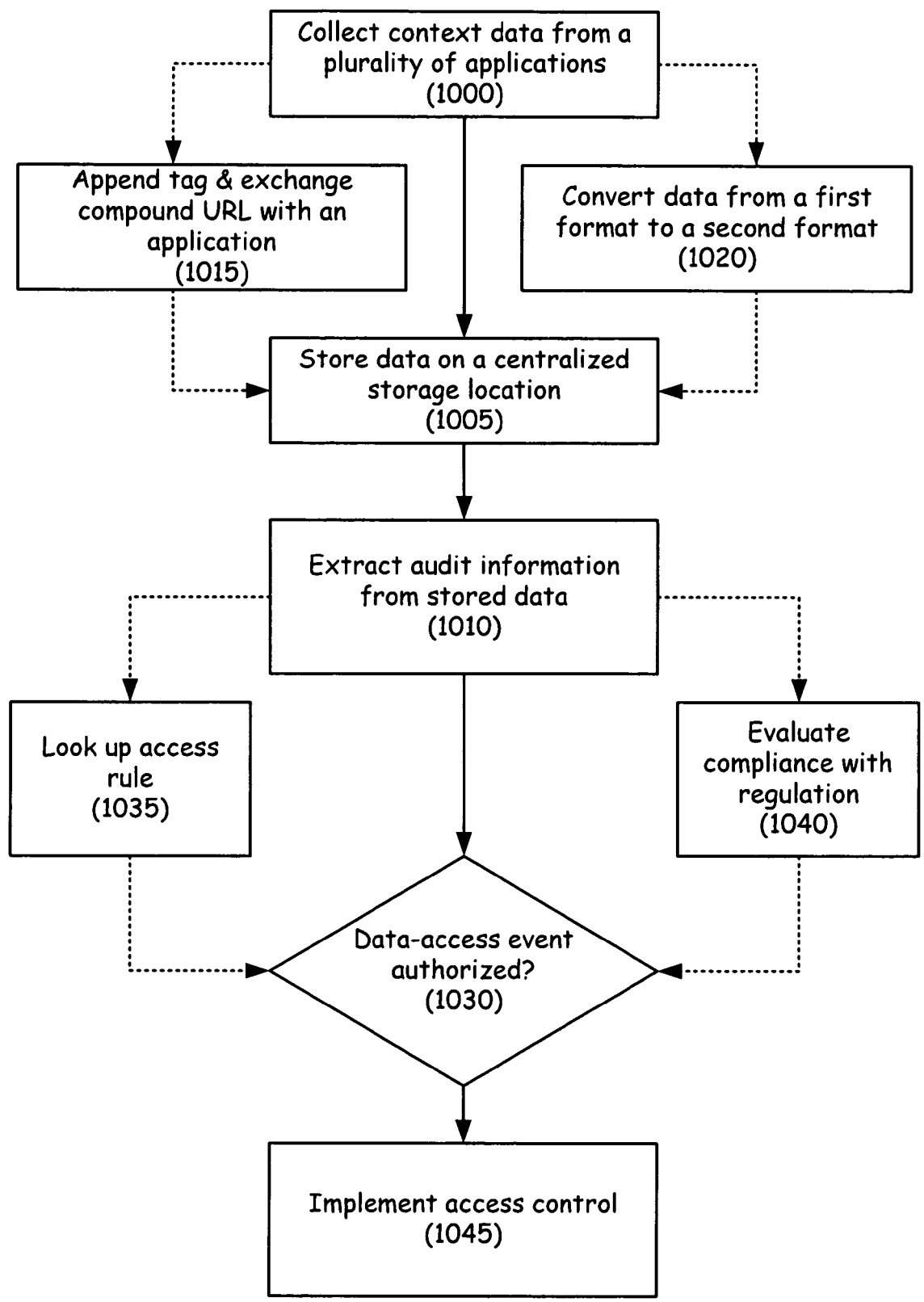
FIG. 11 shows an embodiment of a method for auditing and controlling data-access events.

FIG. 11 shows an exemplary method carried out according to some embodiments of the present invention. In act 1000, context data is collected from a plurality of applications. In act 1005, data corresponding to the collected context data, which may include data identical to the collected context data, is stored on a centralized storage location. Optionally, collecting the context data as in act 1000 may comprise appending and/or exchanging a compound URL with one or more applications, as shown in act 1015. Also, data may be converted between two different data formats, as shown in act 1020.

Once collected data is stored on the centralized storage location, at least a subset of the stored data is extracted and/or processed to obtain audit information according to act 1010.

The extracted data from act 1010 may be used for comparison against a rule available to the context management system, such as a lookup table or an algorithm, in act 1035. The extracted data may also be evaluated for assessing compliance with a policy or regulation, such as the HIPAA, as shown in act 1040.

The exemplary embodiment also shows in act 1030 a determination of whether a particular data-access event is authorized. This is possibly done using an authorizer as part of or in conjunction with the context manager, and may base the determination on a comparison of some data from the context data and the set of rules accessible to the authorizer.

The method also shows, in act 1045, an access control step which can allow or deny execution of an access-control event or act by a user as described earlier. An access controller may be used to enforce the access control and a monitor may be informed or activated responsive to the authorization and access control status.

Figure 12:
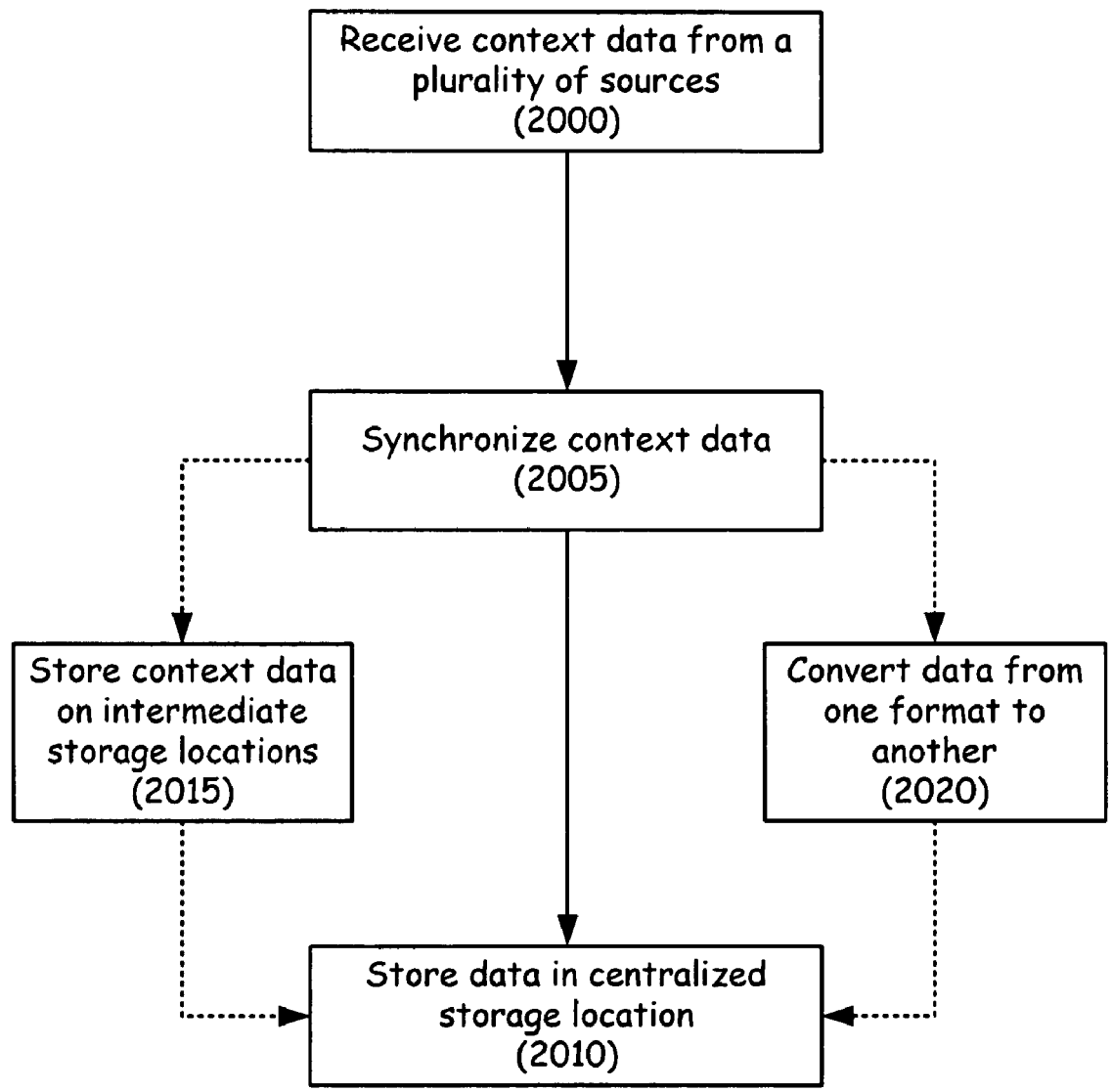
FIG. 12 shows an embodiment of a context data processing and storage method.

FIG. 12 shows an exemplary embodiment of a method for processing context data in a context management system such as those given in the previous discussion. The method comprises receiving context data from a plurality of sources in act 2000. The context data are synchronized according to a synchronization scheme, possibly using a synchronizer, in act 2005. The data having been synchronized is stored in a centralized storage location in act 2010.

Optionally, the data may be stored on intermediate storage locations, which may be clustered storage devices sharing a single directory, as shown in act 2015. Also, the data may be converted between one data format and another as in act 2020 prior to storing onto the centralized storage location.

The CCOW standard supports collections of methods known as interfaces, which include secure and non-secure interfaces. Various methods are carried out by context-enabled applications within the framework of the interfaces. The applications exchange parameters and data with the context manager when using the context management system. The exchanged parameters and data can include application identification (ID) information, Uniform Resource Locators (URLs) and other information. According to the CCOW standard, not all methods are required to provide the identity of the application to the context manager. This can compromise the auditing ability of an auditor by failing to provide all (e.g., application-identifying) data for the activity record or log used by the auditor. A solution to this problem is presented below and briefly explained using exemplary embodiments that are intended to clarify the solution but are not intended to be limiting.

Context-enabled applications almost always invoke a "Join" method, or another identifying method, that includes application-identifying information, prior to beginning context transactions with the context manager. In some embodiments, applications use a Web-based interface to exchange URL data with the context manager in the course of conducting context-related transactions. These applications invoke a method, such as the "Locate" method, which provides them with the location of the context manager or its URL. Other applications, e.g., COM-based applications and non-Web-based applications, do not exchange URL data with the context manager. Even some Web-based applications carry out methods that do not include application-identifying information in their communications.

Accordingly, some embodiments of the present invention are directed to a Web-proxy, e.g., a COM-to-Web proxy, which provides HTTP calls and URLs for identifying those applications which do not normally identify themselves in their communication with the context manager or which are carrying out methods that do not include application-identifying information. The context manager's URL may be augmented or decorated with extra appended information including application-identification "tags." This appended ID tag information may be suitable for identifying the applications where the applications would otherwise be unidentified to the context manager.

One implementation of the above concept involves having the context manager append an ID tag to its URL, thus forming a compound URL. The context manager then passes the compound URL, having the ID tag appended thereto, to the application requesting the context manager's services. The application will then include the compound URL in the communications and request messages and responses it exchanges with the context manager. Since the compound URL includes the ID tag information, the context manager will be able to associate, e.g., using a lookup table, which application is conducting a given context transaction or method, even if the method does not explicitly require the use of application-identifying information.

It should be understood that this concept is not limited to CCOW COM-based applications, but can be extended to other Web-based and non-Web-based applications as well. In addition, it should be understood that a compound URL can be formed by including or appending URL data that not only signifies application-identifying information, but also can carry out an unlimited number of other useful auxiliary functions that require passing data between an application invoking a method and the context manager. This means that applications are not limited to exchanging the information defined by the method, but rather, by using the proxy, the applications can exchange a broad spectrum of information with the context manager. Some of this augmenting information carried in the compound URL may then be used for audits or other functions, or may be passed on to other applications.

Figure 13:
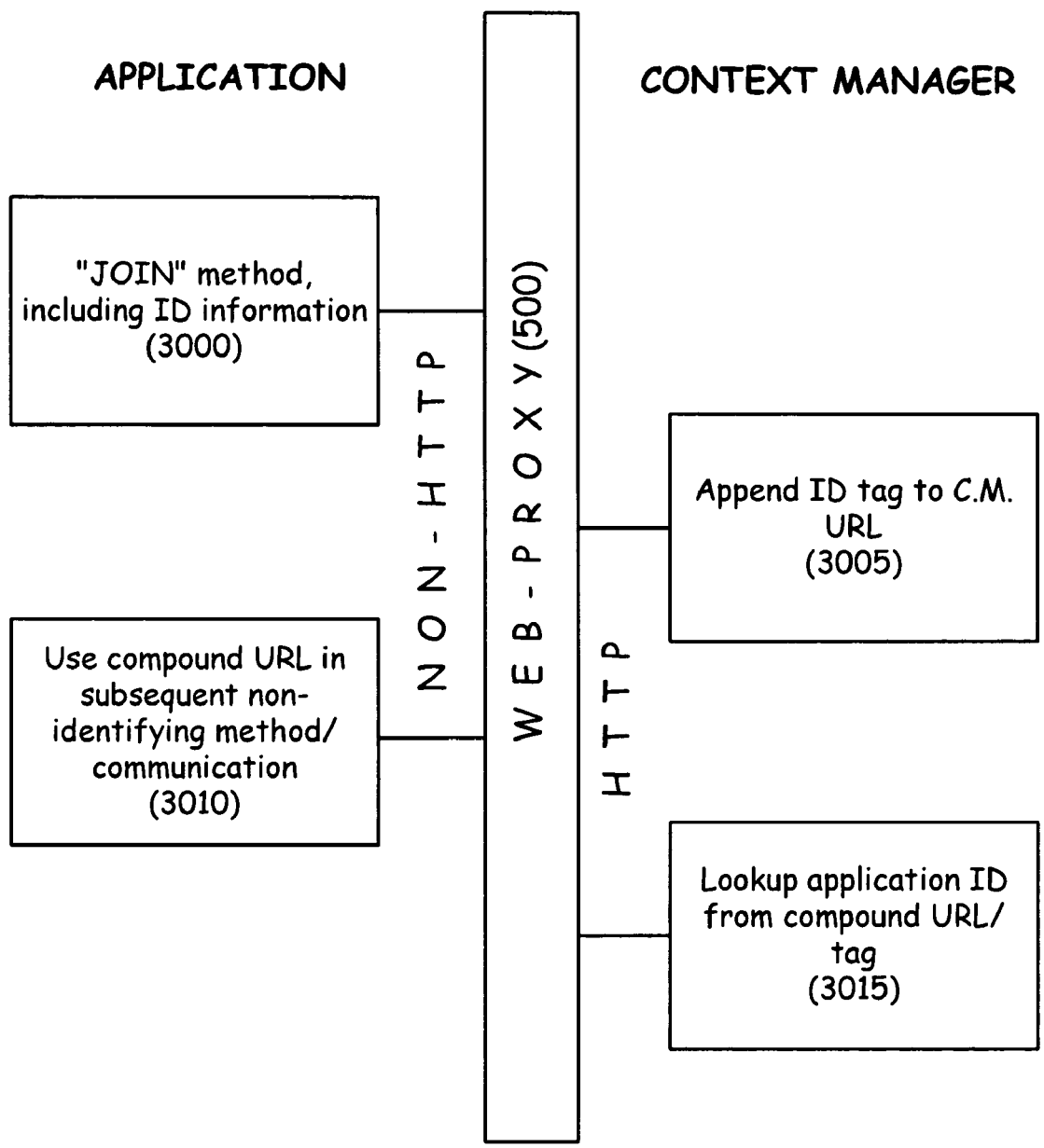
FIG. 13 shows an embodiment of a context management system using a COM-to-Web proxy.

FIG. 13 shows an embodiment of a context management system using a COM-to-Web proxy 500 for allowing the context manager to identify communications from a non-Web-based application 111 that does not provide its identity to the context manager 100. The context manager 100 exchanges information, including URL information 510 and URL-augmenting information 520 through a Web interface 540 with context-enabled applications 111, 113. A first application is a Web-based application 113 and exchanges URL information 510 with the context manager as usual. Other information customary to the various method operations is not shown in the figure.

A second application is a non-Web-based application 111. This application exchanges information, including a compound URL 525, consisting of URL information 510 and URL-augmenting information 520, with the COM-to-Web proxy 500. The COM-to-Web proxy 500 handles the communication with the Web interface 540. The system thus even supports applications that would normally not identify themselves, and the context manager according to this embodiment can determine the identity of any such applications, even if they are using methods which normally would not include application-identifying information.

Figure 14:
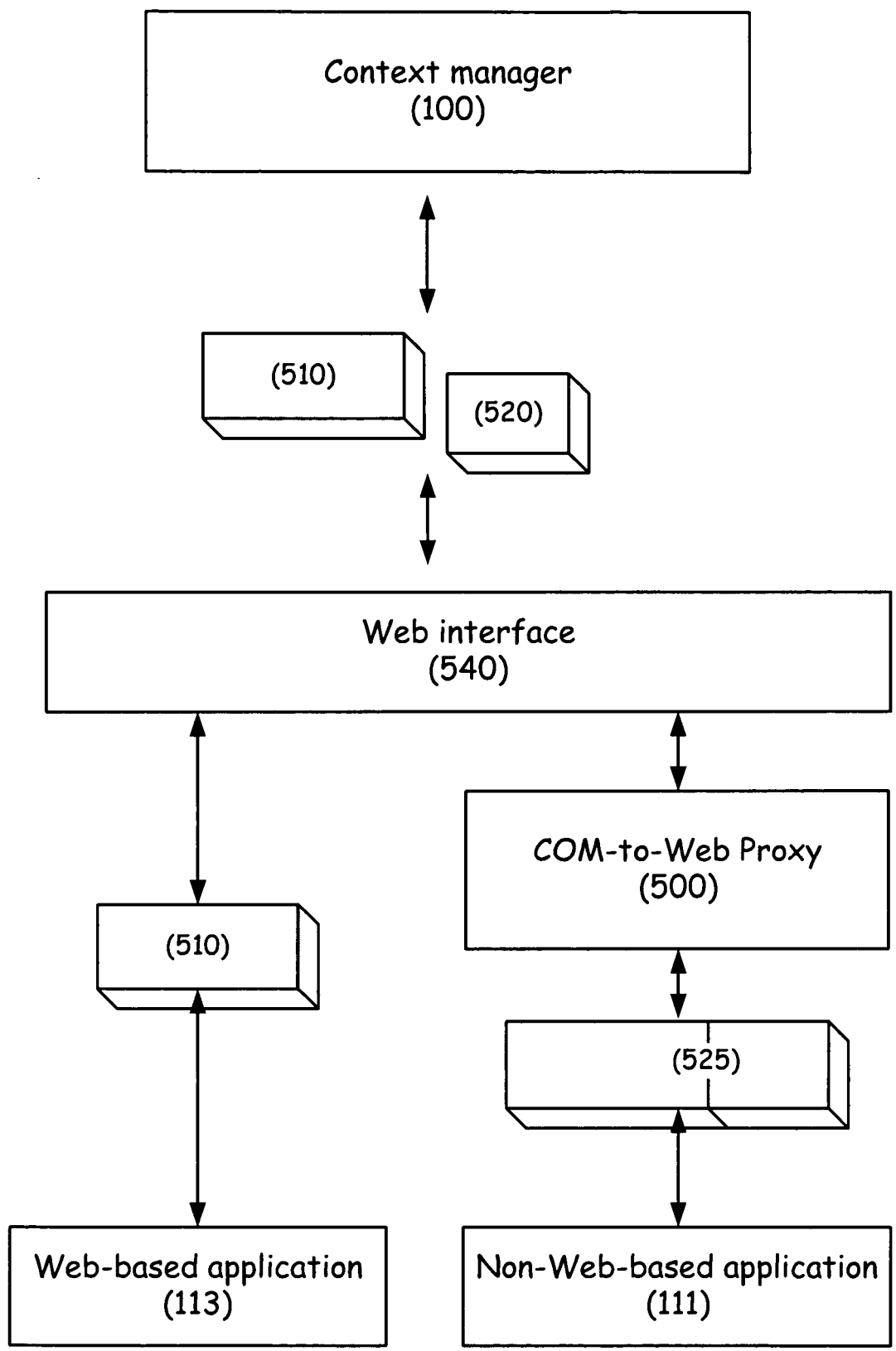
FIG. 14 shows a simplified embodiment of a method for communication and for identification of an application using a Web-proxy.

FIG. 14 shows a method carried out in a multi-layer context management environment. Here a Web-proxy is used to convert communications from a first non-Web-based layer, using a non-HTTP protocol, to and from a second, Web-based, layer using the HTTP protocol. In act 3000, a non-Web-based application uses a "Join" method that includes application-identifying information. The context manager appends an ID tag in act 3005 to the context manager's URL to yield a compound URL which will identify the application in future transactions with the context manager. The application uses the compound URL for subsequent communications through the Web-proxy to the context manager in act 3010. These communications now having the ID tag appended thereto in a way that allows the context manager to identify the application, possibly using a lookup table, as in act 3015.

Figure 15:
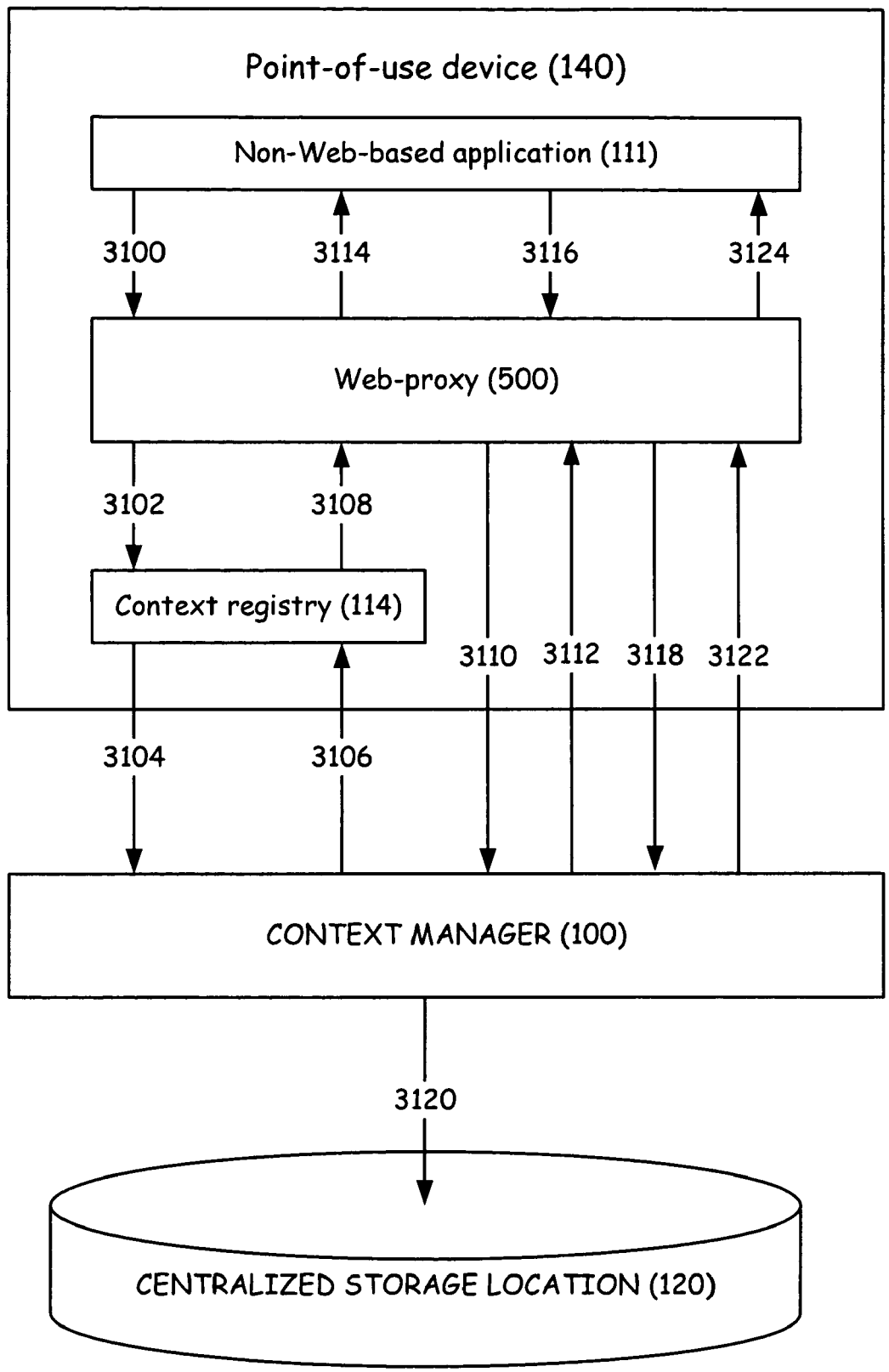
FIG. 15 shows an exemplary embodiment of a system using a Web-proxy to handle context management communications with a non-Web-based application.

FIG. 15 shows a context management system and sequence of acts and/or communications according to one embodiment of the present invention. A point-of-use device 140 has a non-Web-based application 111 and a Web-proxy 500 and a CCOW context registry 114 executing thereon. Communications are carried out with a context manager 100 coupled to a centralized storage location 120 such as a database.

A "Join" method is invoked and an application-identifying signal 3100 is sent from the non-Web-based application 111 to the Web-proxy 500. The Web-proxy 500 sends a "Locate" signal or method communication 3102 to the CCOW context registry 114. Next, the CCOW context registry 114 obtains the context manager's URL by sending a signal 3104 and receiving a signal 3106 comprising the compound URL with an application ID tag. Resources are also allocated for the application 111 by the context manager 100.

The Web-proxy 500 sends a "Join" signal 3110 to the context manager 100, which associates the application 111 identity with the ID tag and returns a coupon to the Web-proxy 500 in signal 3112. The coupon is given to the application 111 by the Web-proxy 500 in signal 3114.

Subsequently, the application 111 may invoke non-identifying methods with signal 3116. The information therein is sent to the context manager 100 in signal 3118. A return from the context manager 100 is provided to the application 111 via the Web-proxy 500 in signals 3122 and 3124, respectively.

Note that the context manager 100 records the application 111 requests and other information onto the centralized storage location 120 as described in previous embodiments.

Figure 16:
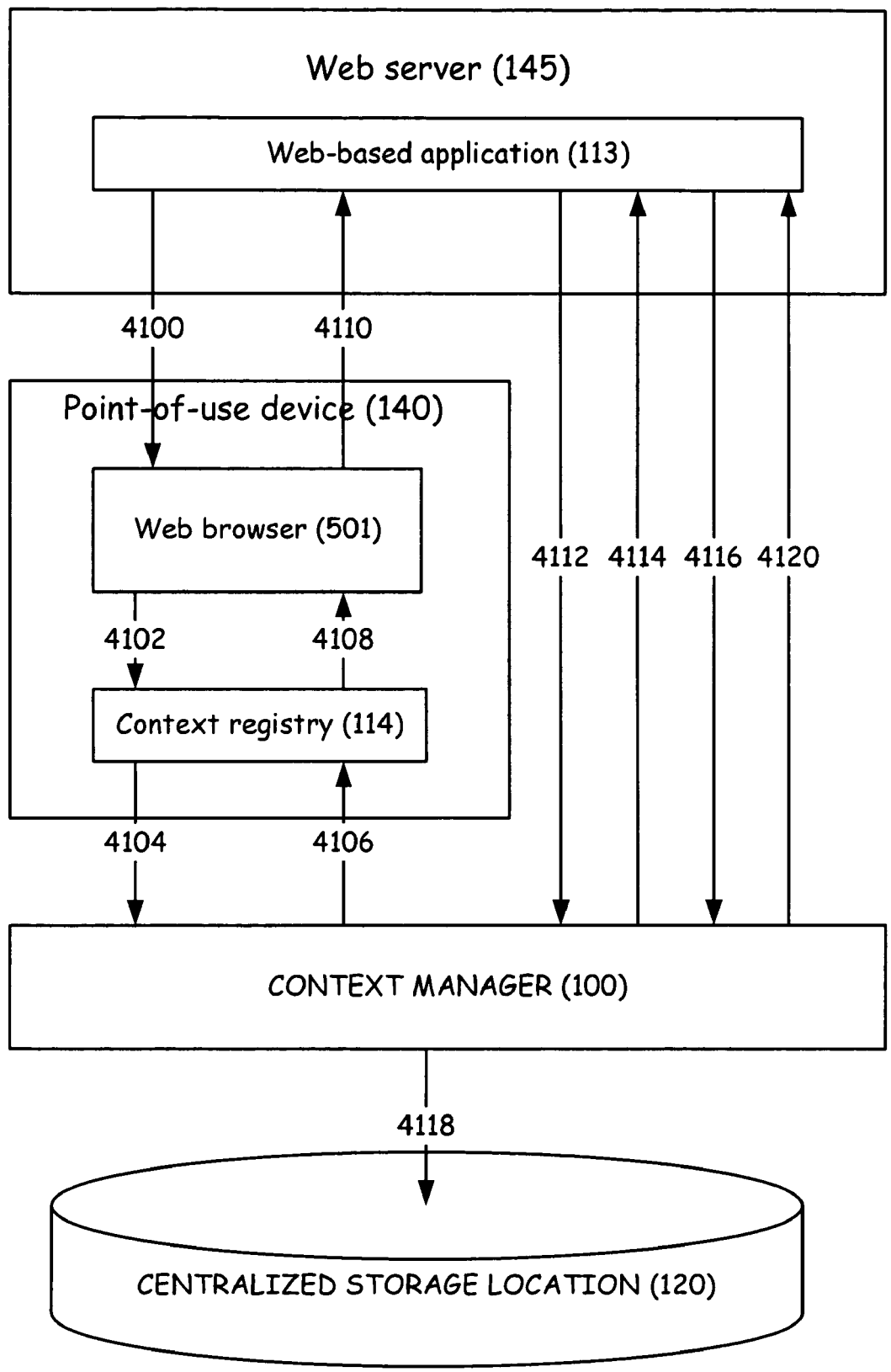
FIG. 16 shows an exemplary embodiment of a system using a Web browser to handle context management communications with a Web-based application.

FIG. 16 shows an exemplary diagram with elements and signals for carrying out a method according to the present invention used by Web-based applications using non-identifying methods.

A Web-server 145 executing a Web-based application 113 is linked with a context manager 100 and a point-of-use device 140 executing a Web browser 501 and a CCOW context registry 114.

On initiating activity, such as by using a "Start Page" event 4100, the Web browser 501 uses a "Locate" method via the CCOW context registry 114 to obtain the context manager's URL and an application ID tag in a compound URL in signals 4102, 4104 and 4106. The compound (or decorated) URL is returned to the Web browser 501 in signal 4108, which is in turn returned to the application 113 in signal 4110. The application 113 can use a "Join" method in 4112 to get a coupon from the context manager 100 in signal 4114. Once it receives the coupon, the application 113 is free to carry out non-identifying methods in communications carrying the compound URL and the ID tag information in signals 4116 and 4120.

As before, the context manager 100 records the application 113 requests and other information onto the centralized storage location 120.

Therefore, and in view of the above description and accompanying drawings, a context management framework is given that provides in various embodiments, numerous advantages over previously-existing systems. In some instances, an architecture having a centralized storage location coupled to a context manager is provided for servicing and logging context events from a plurality of sources. This type of system uses a synchronization scheme to perform orderly storage and retrieval of data to and from the centralized storage location. In other instances, information stored in the centralized storage location or signals from the context manager are used to achieve an auditing capability for reviewing and acting on context data events and gestures. Selective blocking or allowance of impending context gestures is accomplished based on a rule set or lookup table containing rules or other data to make such access control decisions. Access to sensitive data and other security measures may thus be implemented using the teachings presented herein.

Having thus described at least one illustrative embodiment of the invention, various alterations, modifications, and improvements will readily occur to those skilled in the art. Such alterations, modifications, and improvements are intended to be part of this disclosure, and are intended to be within the spirit and scope of the invention. Accordingly, the foregoing description is by way of example only and is limited only as defined in the following claims and the equivalents thereto.

What is claimed is:

1. A computer-implemented method for auditing data-access events occurring in a context management system, the method comprising:
   (A) collecting context data from a plurality of applications that use the context management system;
   (B) storing data corresponding to the collected context data on a centralized storage location; and
   (C) extracting audit information by processing at least a subset of the data stored on the centralized storage location,
   wherein the context data comprises patient context data items; and
   wherein the method further comprises:
   (D) appending an application-identifying tag to a URL to yield a compound URL; and
   (E) exchanging the compound URL with an application such that future communications with the application allow a context manager to identify the application from the application-identifying tag.

2. The method of claim 1, wherein any of the plurality of applications supports the CCOW standard set.

3. A computer-implemented method for assessing compliance with the HIPAA, in a context management system, the method comprising:
   (A) collecting context data from a plurality of applications that use the context management system;
   (B) storing data corresponding to the collected context data on a centralized storage location; and
   (C) extracting audit information by processing at least a subset of the data stored on the centralized storage location, the audit information suitable for making an assessment of compliance with a provision of the HIPAA;
   wherein any of the plurality of applications supports the CCOW standard set.

4. The method of claim 3, wherein the audit information comprises application-identifying information.

5. The method of claim 3, wherein the data corresponding to the collected context data is the same as the context data.

6. The method of claim 3, wherein the context management system supports the CCOW standard set.

7. The method of claim 3, wherein the context data is formatted according to the CCOW standard set.

8. The method of claim 3, further comprising, prior to (B), converting the context data between a first format, complying with the CCOW standard set, and a second data format.

9. The method of claim 3, wherein at least a first application executes on a first machine at the point-of-use and at least a second application executes on a second machine.

10. The method of claim 3, wherein at least a first application executes on a first machine comprising a remote server and at least a second application executes on a second machine.

11. The method of claim 3, wherein at least two applications execute on a same machine.

12. The method of claim 3, wherein a first application and a second application are each separate instances of the same application executing simultaneously.

13. The method of claim 3, wherein a first application and a second application are two different applications executing simultaneously.

14. The method of claim 3, wherein the processing in (C) comprises querying the data stored in the centralized storage location.

15. The method of claim 3, wherein the method is performed by software executing on a machine coupled to the centralized storage location over a network.

16. The method of claim 3, wherein the method is performed by software executing on a machine housing the centralized storage location.

17. The method of claim 3, wherein (B) comprises:
   (i) storing the context data onto an intermediate collection platform, disposed between the context management system and the centralized storage location; and
   (ii) sending the context data from the intermediate collection platform to the centralized storage location.

18. The method of claim 17, wherein the intermediate collection platform comprises a message queue.

19. The method of claim 17, wherein the intermediate collection platform comprises a storage buffer.

20. The method of claim 3, further comprising, following (C):
   (D) based on the extracted audit information, determining whether a data access event is authorized under a set of access control rules.

21. The method of claim 20, further comprising, following (D):
   (E) preventing execution of the data access event if the data access event is not authorized.

22. The method of claim 20, further comprising, following (D):
   (E) sending a message to a monitor, indicating an attempt to execute the data access event.

23. The method of claim 22, wherein the monitor is at least one of: an electronic mail server, a telephony server, a paging server, a portable communicator, an alarm device and a human operator.

24. The method of claim 20, wherein the set of access control rules is accessible to the context management system.

25. The method of claim 3, wherein the method is performed by software, execution of which is not subject to preemption by a user.

26. The method of claim 3, wherein the centralized storage location is a database.

27. The method of claim 3, further comprising:
(D) passing the context data between a first application and a second application using a context manager.

28. The method of claim 3, further comprising:
(D) collecting active-application data indicative of which of the plurality of applications is in immediate use by a user.

29. The method of claim 3, further comprising, prior to (C):
(D) granting an authorized auditor access to the centralized storage location.

30. The method of claim 3, further comprising, prior to (C):
(D) collecting point-of-use data identifying a point-of-use machine.

31. The method of claim 3, further comprising:
(D) evaluating the audit data to make an assessment of compliance with a set of regulations.

32. The method of claim 31, wherein the set of regulations corresponds to the HIPAA.

33. The method of claim 3, wherein (B) comprises storing of the context data according to a synchronization scheme that combines into the centralized storage location context data from at least two sources.

34. The method of claim 3, wherein the plurality of applications exchange context data through a context manager operating in a healthcare facility and the context data relates to patient records.

35. A computer-implemented data processing system for auditing data access events in a context management framework, comprising:
a plurality of software applications executing in the data processing system;
a context manager coupled to the software applications that manages context data exchanges between the software applications;
a centralized storage location, coupled to the context manager, that stores a central record of the context data exchanges; and
an auditor, coupled to the centralized storage location, that retrieves information from the centralized storage location indicative of data access events occurring in the data processing system,
wherein the software applications comply with the CCOW standard set; and
wherein the data processing system further comprises a data formatter, arranged to convert data passing between the context manager and the centralized storage location between a first format, supported by the CCOW standard set, and a second format.

36. The system of claim 35, further comprising a message dispatcher that sends a message to a monitor based on an output from the auditor.

37. The system of claim 36, wherein the monitor comprises at least one of: an electronic mail server, a telephony server, a paging server, a portable communicator, an alarm device and a human operator.

38. The system of claim 35, further comprising an authorizer that determines whether a data access event is authorized.

39. The system of claim 38, further comprising an access controller that controls data-access events responsive to an output from the authorizer.

40. The system of claim 35, wherein the centralized storage location comprises a database.

41. The system of claim 35, further comprising a plurality of clustered storage locations sharing a common index, the clustered storage locations holding data used by the context manager.

42. The system of claim 35, further comprising an intermediate collection platform disposed between the context manager and the centralized storage location.

43. The system of claim 42, wherein the intermediate collection platform comprises a message queue.

44. The system of claim 42, wherein the intermediate collection platform comprises a storage buffer.

45. The system of claim 35, further comprising means for blocking execution of a data-access event on a machine coupled to the system.

46. The system of claim 35, further comprising a Web-proxy that converts communications between a first, World Wide Web-based, format and a second format.

47. The system of claim 46, wherein the second format is COM-based.

48. The system of claim 46, further comprising a Web interface coupled between the context manager and the Web-proxy.

49. A machine-readable storage medium having thereon instructions, which when executed by at least one computer:
(A) collect context data from a plurality of applications that use a context management system;
(B) store data corresponding to the collected context data on a centralized storage location; and
(C) extract audit information by processing at least a subset of the data stored on the centralized storage location,
wherein any of the plurality of applications supports the CCOW standard set; and
wherein the machine-readable storage medium further comprises instructions
which, when executed:
(D) convert context data from a first data format to a second data format.

50. The machine-readable storage medium of claim 49, wherein any of the first and second data formats is according to the CCOW standard set.

51. The machine-readable storage medium of claim 49, wherein the centralized storage location comprises a database.

52. The machine-readable storage medium of claim 49, wherein (B) comprises sending data over a network coupling the context manager and the centralized storage location.

53. The machine-readable storage medium of claim 49, further having instructions, which when executed:
(D) couple application-identification information to a URL being delivered through the context manager.

54. The machine-readable storage medium of claim 49, further having instructions, which when executed:
(D) determine whether a data-access event is authorized under a set of access control rules.

55. The machine-readable storage medium of claim 49, further having instructions, which when executed:
(E) prevent execution of the data-access event if the data-access event is not authorized.

56. The machine-readable storage medium of claim 49, further having instructions, which when executed:
(E) send a message to a monitor, indicating an attempt to execute the data-access event.

57. The machine-readable storage medium of claim 56, wherein the monitor is at least one of: an electronic mail server, a telephony server, a paging server, a portable communicator, an alarm device and a human operator.

58. The machine-readable storage medium of claim 54, wherein (D) comprises comparing context data to a rule available to the context manager.

59. The machine-readable storage medium of claim 49, wherein execution of the instructions is performed by software, execution of which is not subject to preemption by a user.

60. A computer-implemented method for identifying an application in a context management environment, wherein the application is coupled to a context manager, comprising:
(A) associating the application with an information tag when the application invokes a method that carries application-identifying information;
(B) augmenting a URL, passing between the context manager and the application, with the information tag, yielding a compound URL containing the URL and the information tag;
(C) parsing a communication from the application containing the compound URL to extract information corresponding to the information tag therefrom when the application invokes a method that does not carry application-identifying information;
(D) looking up the identity of the application corresponding to the information tag; and
(E) convening communications between a first Web-based format and a second format.

* * * * *